US012714500B2

(12) United States Patent
Artzi et al.

(10) Patent No.: US 12,714,500 B2
(45) Date of Patent: Aug. 25, 2026

(54) DEVICES, METHODS, AND SYSTEMS FOR SCREW PLANNING IN SURGERY

(71) Applicant: Mazor Robotics Ltd., Caesarea (IL)

(72) Inventors: Dor Artzi, Tel Aviv-Jaffa (IL); Yizhaq Shmayahu, Ramat HaSharon (IL); Diego Merkier, Bat Hefer (IL); Or Riven, Haifa (IL); Dany Junio, Tel Aviv-Jaffa (IL); Aviv Ellman, Kfar Sava (IL); Leon Kleyman, Misgav (IL)

(73) Assignee: Mazor Robotics Ltd., Caesarea (IL)

( * ) Notice: Subject to any disclaimer, the term of this patent is extended or adjusted under 35 U.S.C. 154(b) by 1074 days.

(21) Appl. No.: 17/671,117

(22) Filed: Feb. 14, 2022

(65) Prior Publication Data

US 2022/0280240 A1 Sep. 8, 2022

Related U.S. Application Data

(60) Provisional application No. 63/155,381, filed on Mar. 2, 2021.

(51) Int. Cl.
*G06F 7/48* (2006.01)
*A61B 34/00* (2016.01)
(Continued)

(52) U.S. Cl.
CPC .............. *A61B 34/10* (2016.02); *A61B 34/20* (2016.02); *A61B 34/25* (2016.02); *A61B 34/37* (2016.02); *G06T 7/10* (2017.01); *A61B 2034/104* (2016.02); *A61B 2034/258* (2016.02); *G06T 2207/30012* (2013.01)

(58) Field of Classification Search
CPC ........ A61B 2034/102; A61B 2034/104; A61B 2034/105; A61B 2034/2051; A61B 2034/2055; A61B 2034/258; A61B 34/10; A61B 34/20; A61B 34/25; A61B 34/30;
(Continued)

(56) References Cited

U.S. PATENT DOCUMENTS

| | | |
|---|---|---|
| 7,194,120 B2 | 3/2007 | Wicker et al. |
| 7,996,064 B2 | 8/2011 | Simon et al. |

(Continued)

FOREIGN PATENT DOCUMENTS

| | | |
|---|---|---|
| CN | 109952070 | 6/2019 |
| WO | WO 2020/079598 | 4/2020 |

OTHER PUBLICATIONS

Official Action with Machine Translation for China Patent Application No. 202110931521.9, dated Dec. 3, 2024, 21 pages.

(Continued)

*Primary Examiner* — Nithya J. Moll
(74) *Attorney, Agent, or Firm* — Sheridan Ross PC

(57) ABSTRACT

A device comprises at least one processor and memory including instructions that when executed by the at least one processor cause the at least one processor to: generate, based on at least one image of a spine within a body, a set of possible screw poses for implanting at least one screw into the spine during a surgical procedure; evaluate each possible screw pose based on at least one consideration associated with the surgical procedure; select, based on the evaluation, at least one screw pose from the set of possible screw poses; and output an indication of the selected at least one screw pose to a user interface.

20 Claims, 3 Drawing Sheets

(51) Int. Cl.

| | |
|---|---|
| ***A61B 34/10*** | (2016.01) |
| ***A61B 34/20*** | (2016.01) |
| ***A61B 34/37*** | (2016.01) |
| ***G06T 7/10*** | (2017.01) |

(58) Field of Classification Search

CPC .................... A61B 34/32; A61B 34/37; G06T 2207/30012; G06T 7/10

See application file for complete search history.

(56) References Cited

U.S. PATENT DOCUMENTS

| | | | | |
|---|---|---|---|---|
| 8,112,292 | B2 | 2/2012 | Simon | |
| 8,116,847 | B2 | 2/2012 | Gattani et al. | |
| 8,335,552 | B2 | 12/2012 | Stiles | |
| 8,442,621 | B2 | 5/2013 | Gorek et al. | |
| 8,617,174 | B2 | 12/2013 | Axelson, Jr. et al. | |
| 8,725,235 | B2 | 5/2014 | Gielen et al. | |
| 9,002,076 | B2 | 4/2015 | Khadem et al. | |
| 9,072,531 | B2 | 7/2015 | Fitz et al. | |
| 9,320,569 | B2 | 4/2016 | Lloyd et al. | |
| 9,549,744 | B2 | 1/2017 | Pommer et al. | |
| 9,600,138 | B2 | 3/2017 | Thomas et al. | |
| 10,188,480 | B2 | 1/2019 | Scholl et al. | |
| 10,390,886 | B2 | 8/2019 | Li et al. | |
| 10,561,465 | B2 * | 2/2020 | Scholl | A61B 17/7086 |
| 10,595,941 | B2 | 3/2020 | Herrmann et al. | |
| 10,706,543 | B2 | 7/2020 | Donhowe et al. | |
| 10,709,509 | B2 | 7/2020 | Scholl et al. | |
| 2015/0182288 | A1 * | 7/2015 | Greenwald | A61B 34/20 606/279 |
| 2017/0143426 | A1 | 5/2017 | Isaacs et al. | |
| 2018/0092699 | A1 | 4/2018 | Finley | |
| 2018/0280159 | A1 | 10/2018 | Hunter et al. | |
| 2018/0303552 | A1 | 10/2018 | Ryan et al. | |
| 2019/0029757 | A1 | 1/2019 | Roh et al. | |
| 2019/0069956 | A1 | 3/2019 | Ryan et al. | |
| 2019/0090969 | A1 | 3/2019 | Jarc et al. | |
| 2019/0146458 | A1 | 5/2019 | Roh et al. | |
| 2019/0262084 | A1 * | 8/2019 | Roh | G16H 30/40 |
| 2020/0138518 | A1 * | 5/2020 | Lang | A61B 17/1666 |

OTHER PUBLICATIONS

Huh et al. "Three Dimensional Measurement of Ideal Trajectory of Pedicle Screws of Subaxial Cervical Spine Using the Algorithm Could Be Applied for Robotic Screw Insertion," Journal of Korean Neurosurgical Society, Jul. 2019, vol. 62, No. 4, pp. 376-381.

Lee et al. "Optimal entry points and trajectories for cervical pedicle screw placement into subaxial cervical vertebrae," European Spine Journal, 2011, vol. 20, pp. 905-911.

Stayman et al. "Task-driven source-detector trajectories in cone-beam computed tomography: I. Theory and methods," Journal of Medical Imaging, Apr.-Jun. 2019, vol. 6, No. 2, article 025002, 14 pages.

Vaccaro et al. "Assessment of Surgical Procedural Time, Pedicle Screw Accuracy, and Clinician Radiation Exposure of a Novel Robotic Navigation System Compared With Conventional Open and Percutaneous Freehand Techniques: A Cadaveric Investigation," Global Spine Journal, Oct. 2020, vol. 10, No. 7, pp. 814-825.

Vijayan et al. "Automatic pedicle screw planning using atlas-based registration of anatomy and reference trajectories," Physics in Medicine & Biology, Aug. 2019, vol. 64, No. 16, article 165020, 32 pages.

Official Action with Machine Translation for China Patent Application No. 202110931521.9, dated Apr. 19, 2024, 20 pages.

* cited by examiner

DEVICES, METHODS, AND SYSTEMS FOR SCREW PLANNING IN SURGERY

CROSS REFERENCE TO RELATED APPLICATIONS

This application claims the benefit of U.S. Provisional Application No. 63/155,381, filed on Mar. 2, 2021, and entitled "Devices, Methods, and Systems for Screw Planning in Surgery," which application is incorporated herein by reference in its entirety.

FIELD

The present technology generally relates to devices systems and methods for screw planning in surgery, for example, in spinal surgery.

BACKGROUND

Surgical robots may assist a surgeon or other medical provider in carrying out a surgical procedure or may complete one or more surgical procedures autonomously. Some surgeries (e.g., spinal fusion surgeries) involve placing one or more screws into bony structures of an anatomy.

SUMMARY

Example Aspects of the Present Disclosure Include:

A device according to at least one embodiment of the present disclosure comprises at least one processor and memory including instructions that when executed by the at least one processor cause the at least one processor to: generate, based on at least one image of a spine within a body, a set of possible screw poses for implanting at least one screw into the spine during a surgical procedure; evaluate each possible screw pose based on at least one consideration associated with the surgical procedure; select, based on the evaluation, at least one screw pose from the set of possible screw poses; and output an indication of the selected at least one screw pose to a user interface.

Any of the aspects herein, wherein the instructions include instructions that when executed by the at least one processor cause the at least one processor to control a robotic arm based on the selected at least one screw pose.

Any of the aspects herein, wherein the instructions include instructions that when executed by the at least one processor cause the at least one processor to generate the at least one image by segmenting at least one three-dimensional image of the spine.

Any of the aspects herein, wherein the at least one consideration includes one or more considerations related to safety of the surgical procedure.

Any of the aspects herein, wherein the at least one consideration includes one or more of a skive avoidance consideration, a breach avoidance consideration, a soft tissue pressure consideration, a collision avoidance consideration regarding possible collisions of a surgical tool with at least one anatomical element in the body, reachability, implant proudness, or an incision size consideration.

Any of the aspects herein, wherein the at least one consideration includes one or more considerations not related to safety of the surgical procedure.

Any of the aspects herein, wherein the one or more considerations include at least one surgical preference of a surgeon that performs the surgical procedure.

Any of the aspects herein, wherein the at least one screw includes a plurality of screws, and wherein the selected at least one screw pose includes a selected screw pose for each of the plurality of screws.

Any of the aspects herein, wherein the at least one consideration relates to alignment of a rod with at least two screws of the plurality of screws, wherein the at least two screws mechanically couple to the rod.

Any of the aspects herein, wherein the evaluation includes scoring each of the possible screw poses based on the at least one consideration, and wherein the selected at least one screw pose is selected based on the scoring.

Any of the aspects herein, wherein the at least one consideration includes a plurality of considerations, the plurality of considerations relating to at least one of safety of the surgical procedure, preferences of a surgeon performing the surgical procedure, or a desired alignment of a rod with the at least one screw.

Any of the aspects herein, wherein at least one of the plurality of considerations is weighted.

A system according to at least one embodiment of the present disclosure comprises a user interface; at least one processor; and memory including instructions that when executed by the at least one processor cause the at least one processor to: generate, based on at least one image of a spine within a body, a set of possible screw poses for implanting at least one screw into the spine during a surgical procedure; evaluate each possible screw pose based on at least one consideration associated with the surgical procedure; select, based on the evaluation, at least one first screw pose from the set of possible screw poses; and output an indication of the selected at least one screw pose to the user interface.

Any of the aspects herein, wherein the instructions include instructions that cause the at least one processor to adjust the selected at least one first screw pose based on received input.

Any of the aspects herein, wherein the received input includes surgical preferences for performing the surgical procedure.

Any of the aspects herein, wherein the instructions include instructions that cause the at least one processor to: discard the selected at least one first screw pose in response to input received from a surgeon; automatically select at least one second screw pose from the set of possible screw poses in response to discarding the at least one first screw pose; and output an indication of the selected at least one second screw pose to the user interface.

Any of the aspects herein, further comprising a robotic arm, wherein the instructions include instructions that cause the at least one processor to: receive an indication that the selected at least one second screw pose is acceptable; and control a robotic arm based on the selected at least one second screw pose.

Any of the aspects herein, wherein the robotic arm is controlled to implant the at least one screw into the spine according to the selected at least one second screw pose.

Any of the aspects herein, wherein the at least one consideration includes considerations relating to at least one of safety of the surgical procedure, preferences of a surgeon performing the surgical procedure, or a desired alignment of a rod with the at least one screw.

A method according to at least one embodiment of the present disclosure comprises generating, based on at least one segmented image of a spine within a body, a set of possible screw poses for implanting at least one screw into the spine during a surgical procedure; evaluating each possible screw pose based on at least one consideration associated with the surgical procedure; selecting, based on the evaluation, at least one first screw pose from the set of possible screw poses; and outputting an indication of the selected at least one screw pose to a user interface.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
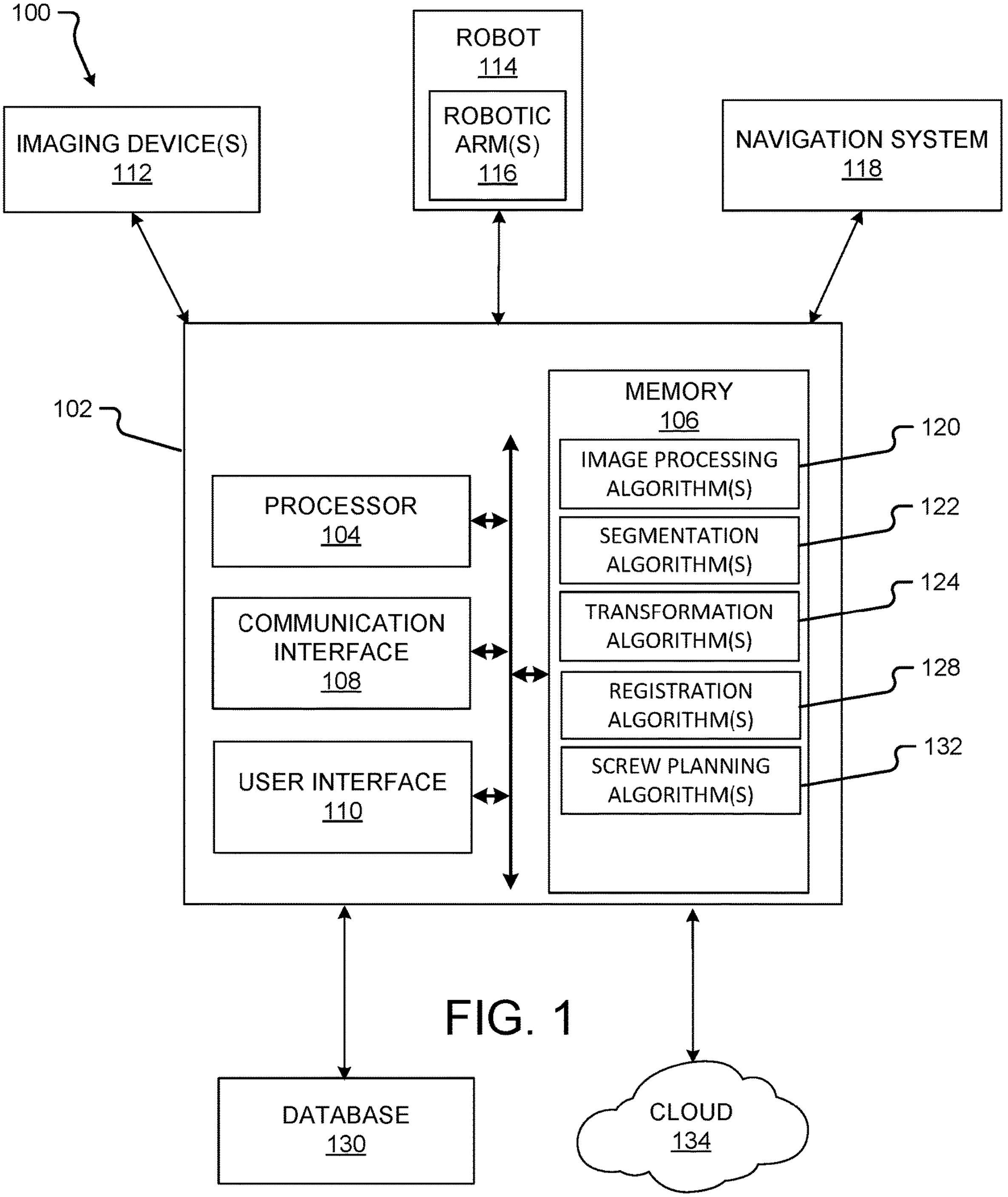
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Robotic insertion of spinal screws may be sensitive to several parameters or considerations that affect the repeatability and/or safety of the procedure. These parameters or considerations include, for example, the potential for skiving, the potential for breaching a sensitive area of the spine with a screw, effects of soft tissue pressure within the anatomy, possible anatomy/tool collision during surgery, reachability, implant proudness, and/or size of skin incision used for the surgery. Embodiments of the present disclosure provide technical solutions for problems related to implanting screws within an anatomy in a safe and predictable manner, where such implantation is performed with or without robotic assistance. For example, inventive concepts relate to improving or optimizing screw planning for a surgical procedure, which may reduce or minimize the learning curve for adopting robotic surgeries, increase the predictability of the procedure, limit clinical complications, and/or improve surgical outcomes. In at least one example embodiment, one or more images of the anatomy undergoing the screw implantation are segmented and possible screw poses are determined based on the segmented image, the above-mentioned considerations, and/or preferences of a surgeon performing or overseeing the surgical procedure. In some cases, the surgeon may be capable of adjusting the planned screw pose, in which case the system provides immediate feedback on potential effects of the adjustment.

In at least one example embodiment, one or more 3D images of a spine are subjected to a bone segmentation process to produce a 3D segmented image that identifies and labels the individual bones of the spine, which is useful for determining possible screw poses for implanting screw into the spine. As noted above and below, each possible screw pose may be evaluated in view of one or more considerations or parameters, which may include the potential for skiving, the potential for breaching a sensitive area of the spine with a screw, effects of soft tissue pressure within the anatomy, possible anatomy/tool collision during surgery, reachability, implant proudness, and/or size of skin incision used for the surgery.

In view of the instant disclosure, it should be appreciated that at least one example embodiment relates to a system that imports a computed tomography (CT) image of a patient's spine and carries out a bone segmentation algorithm on the CT image. If the segmentation is not successful, the method disables the screw planning feature and ends. If, however, the segmentation is successful, the method may proceed to generate an initial screw pose recommendation per pedicle. Then, user or surgeon preferences may be applied to the initial screw pose recommendations before searching for potential solutions for each pedicle. Upon arriving at potential solutions for each pedicle, the method may run a go/no-go check for each solution to remove invalid solutions from the list of possible solutions (where invalid solutions include solutions that do not meet a minimum threshold or that violate one or more rules for the surgical procedure). Thereafter, the method may include prioritizing or scoring all valid solutions per screw where the valid solutions are solutions that were determined to be a 'go.' Following prioritization, the method may select an optimal solution for each screw, which may include considerations regarding the curvature of a rod that mechanically couples to the screw. Finally, the method may include displaying the solutions for each screw for review and/or approval by the user.

Turning first to FIG. 1, a block diagram of a system 100 according to at least one embodiment of the present disclosure is shown. The system 100 may be used to assist with planning screw poses for implant into an anatomy and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200 and 300 described herein, or of any other methods. The memory 106 may store, for example, one or more image processing algorithms 120, one or more segmentation algorithms 122, one or more transformation algorithms 124, one or more registration algorithms 128, and/or one or more screw planning algorithms 132 (see FIGS. 2 and 3, for example). Such instructions or algorithms may, in some embodiments, be organized into one or more applications, modules, packages, layers, or engines. The algorithms and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving data or information from an external source (such as the imaging device 112, the robot

114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device 112 may provide first image data and/or a first image, and a second imaging device 112 may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The system 100 or similar systems may be used, for example, to carry out one or more aspects of any of the methods 200 and 300 described herein. The system 100 or similar systems may also be used for other purposes.

Figure 2:
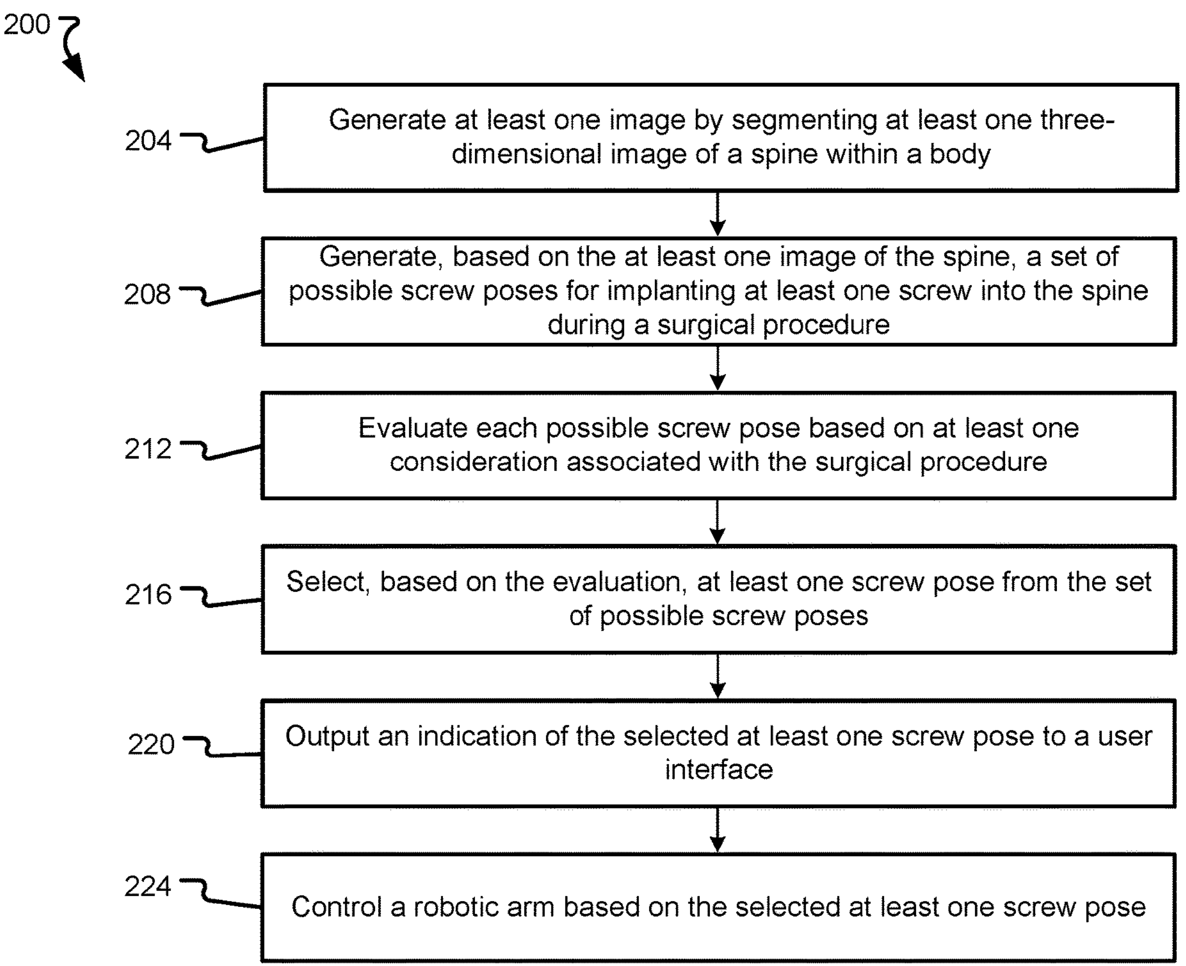
FIG. 2 is a flowchart according to at least one embodiment of the present disclosure.

FIG. 2 depicts a method 200 that may be used, for example, to assist with planning implantation of screws in an anatomy such as a spine.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing instructions stored in a memory such as the memory 106. The instructions may correspond to one or more steps of the method 200 described below. The instructions may cause the processor to execute one or more algorithms, such as an image processing algorithm 120, a segmentation algorithm 122, a transformation algorithm 124, a registration algorithm 128, and/or a screw planning algorithm 132.

The method 200 comprises generating at least one image by segmenting at least one three-dimensional image of a spine within a body (step 204). For example, operation 204 includes subjecting one or more 3D images of the spine taken in an MRI scan and/or a CT scan to a suitable bone segmentation process. The resulting segmented image may be further analyzed to identify and label parts of the spine and/or other anatomies and/or to derive one or more characteristics about the parts of the spine or other anatomies such as bone and/or tissue densities, bone dimensions, relative bone dimensions, bone locations, relative bone locations, bone geometry, and/or the like. The resulting segmented image may be displayed on the user interface 110 along with the above-described information. Here, it should be appreciated that step 204 may alternatively generate the at least one image by a suitable method other than segmentation so long as the method produces the at least one image in a manner that is still usable for remaining steps of the method 200 and/or steps of the method 300.

The method 200 also comprises generating, based on the at least one image of the spine, a set of possible screw poses for implanting at least one screw into the spine during a surgical procedure (step 208). The at least one screw may include a cortical screw, a pedicle screw, and/or other suitable screw or mechanical fixing device (e.g., a staple, a pin, and/or the like). A screw pose refers to the position and orientation of the screw as it is implanted into bone or another anatomical element. The position and orientation, or pose, may be expressed with respect to a Cartesian coordinate system and spherical coordinate system. A proper screw pose is useful for reducing or avoiding collateral damage to parts of the anatomy when implanting the screw and/or for achieving the desired outcome of the surgical procedure (e.g., by having screws properly secured to the bone, properly aligned and connected to a rod, and so forth). Step 208 may determine the set of possible screw poses based at least in part on real-time input and/or preprogrammed input from the surgeon that indicates which sections of the spine (e.g., which vertebra or vertebrae) are subject to screw implantation during the surgical procedure.

In some embodiments, a surgeon or other user may propose a first screw pose or multiple screw poses, after which the set of possible screw poses may be determined based on the first screw pose or multiple screw poses. In other embodiments, a first screw pose may be generated automatically based on, for example, the segmented image resulting from the step 204 and/or on one or more preprogrammed data points regarding possible screw poses.

The set of possible screw poses may be generated based on information generally known to be desired for successful screw implantation, which may include information about generally acceptable ranges of angles for implantation, generally acceptable locations for screw implantation, generally used screw types and sizes, and/or other suitable general knowledge for the surgical procedure. In at least one example embodiment, the set of possible screw poses may be generated based on knowledge gained from a prior similar surgical procedure performed on the same spine or on one or more different spines (e.g., of other patients). For example, the set of possible screw poses may be generated with the assistance of artificial intelligence executing one or more machine learning algorithms that have been trained with training data, where the training data includes data from previous surgeries on spines or other parts of an anatomy. In some cases, a pose of one screw may affect a pose of one or more other screws (e.g., when two or more screws should be aligned and mechanically coupled to a rod). Thus, each possible screw pose for a particular screw may be determined based on one or more of the possible screw poses for other screws.

Step 208 may generate any number of possible screw poses for each screw planned for implantation. Thus, the number of possible screw poses for each screw may be too great to analyze efficiently. For example, the set of possible screw poses may include tens, hundreds, or thousands of possibilities. Accordingly, the method 200 includes evaluating each possible screw pose based on at least one consideration associated with the surgical procedure (step 212) and selecting, based on the evaluation, at least one screw pose from the set of possible screw poses (step 216). Steps 212 and 216 may occur automatically after step 208 and may be useful for automatically reducing the number of possible screw poses generated in step 208 to a more manageable number by using the evaluation to reject possible screw poses that are unworkable (e.g., fail to meet a predetermined threshold) in light of the at least one consideration. As discussed in more detail below, evaluating the set of possible screw poses may include scoring each possible screw pose based on the at least one consideration and the screw pose with a highest score may be selected. In embodiments where the at least one consideration comprises a plurality of considerations, the scoring may involve weighting one or more of the plurality of considerations. Additionally, in some embodiments, one or more of the at least one consideration may be or comprise a binary determination (e.g., whether the pose results in the screw penetrating a vertebral endplate), while others of the one or more consideration may be scored along a numerical or other scale. The screw pose selected in operation 216 may be an optimal screw pose for a set of considerations and/or surgeon preferences.

In at least one example embodiment, the at least one consideration on which the evaluation in step 212 is based includes a skive avoidance consideration, a breach avoidance consideration, a soft tissue pressure consideration, a collision avoidance consideration regarding possible collisions of a surgical tool with at least one anatomical element in the body, reachability, implant proudness, and/or an incision size consideration. These considerations are discussed in more detail below.

Skiving refers to a scenario where a tool used for implanting the screws, such as a drill, slips or otherwise moves away from a target implant location on a bony structure of the spine during operation (e.g., a target location on a vertebra), thereby posing a risk to safety and/or the overall success of the surgery. The slippage may be due to a contour of the target implant location. Ideally, a surface contour of the target location and the tip of the drill or other tool for implanting screws form a substantially 90-degree angle so as to avoid skiving during screw implantation. However, the contour of the target implant location may not allow for the drill or other tool to form the ideal angle with the surface of the target location, thus introducing the possibility of skiving. Accordingly, evaluating the set of possible screw poses based on a skive avoidance consideration may reduce the risk of skiving by, for example, preventing selection of (or providing warnings about) screw poses that have an unacceptably high risk of skiving.

For example, using the segmented image from operation 204, the method 200 may determine whether a drill bit being used to drill a hole to accommodate a particular screw pose will form an unacceptable angle with the surface contour of the target implant location, and use the determination to rank the particular screw pose in a manner that affects the possibility for selection in step 216. In general, the risk of skiving increases as the angle between the tool and the surface contour of the target implant location moves away from 90 degrees. Thus, the ranges of acceptable angles and unacceptable angles may be a design parameter set based on empirical evidence and/or preference. In the event that skiving cannot be avoided for the possible set of screw poses, then the method 200 may including outputting an indication to the user interface 110 to inform the surgeon that skiving may occur, which the surgeon can use to prepare for surgery by equipping tools to flatten the target implant location and/or by being cognizant of possible skiving during surgery.

Breaching refers to a scenario where a screw breaches or exits the vertebral body or other part of the anatomy receiving the screw. Such a breach may risk damage to nerves and/or other anatomical elements proximate the breached part of the screw. Parameters that affect whether a screw breaches include screw length, screw width, screw implant angle, screw implant depth, vertebral geometry (where the screw is being implanted in a vertebra), and/or the like. Accordingly, evaluating the set of possible screw poses based on a breach avoidance consideration may reduce the risk of screw breach by, for example, preventing selection of or providing warnings about screw poses that have an unacceptably high risk of breaching.

Soft tissue pressure may refer to pressure induced on a screw (and/or on a tool being used to prepare for implantation of the screw) by surrounding soft tissue. During surgery, soft tissue is often moved aside by retractors. However, soft pressure may affect various parameters of screw implantation such as the implantation angle of the screw, irritation of the soft tissue by the screw post implantation, and/or the like. More retraction may increase the risk that some portion of the soft tissue contacts an upper portion of the screw (e.g., after screw implantation), affecting the angle or implant state of the screw. In general, smaller axial angles of screw implantation are associated with smaller chances for the screw angle being affected by soft tissue pressure. Soft tissue pressure information may be derived from an image obtained with an MRI scan. Thus, in at least one example embodiment, the method 200 includes co-registering an image from a CT scan (used for bone segmentation) with an image from an MRI scan to gather information about soft tissue pressure for the set of possible screw poses and using the information in the evaluation of step 212.

As may be appreciated, surgery, whether robot assisted or not, involves navigating or otherwise moving one or more tools to a target site within a larger anatomy. Accordingly, the possibility exists for collisions between a tool and another tool or between a tool and one or more anatomical elements (e.g., a spinous process) that are not part of the target site. Evaluating the set of possible screw poses in view of a collision avoidance consideration may reduce the risk of undesired collisions between tools or between tools and parts of the anatomy, thereby increasing safety of the procedure and/or enhancing the procedure's outcome.

The at least one consideration may include a reachability consideration, which the method 200 may use to determine how difficult it would be for a tool to reach a particular target implant location to prepare for implantation of and/or implant a screw. Reachability may be negatively impacted by parts of the anatomy surrounding a target implant location. In other words, reachability may be an assessment of how much one or more parts of the anatomy in proximity to the target implant location would interfere with screw implantation. Evaluating screw poses in view of reachability may reduce the time taken for the surgical procedure in that unreachable screw poses may be excluded from selection in step 216.

Implant proudness may refer to the amount of protrusion of a screw from an implant site and/or a depth of the screw in the implant site. For example, if the screw is buried too deep into a pedicle, then movement of the tulip of the screw may be hindered or prevented. On the other hand, a screw protruding too far from a pedicle may interfere with rod alignment, suffer from soft tissue pressure problems, and/or irritate surrounding parts of the anatomy. Accordingly, evaluating the set of possible screw poses according to an implant proudness consideration may avoid issues stemming from a screw being implanted too deep or too shallow at the implant site.

An incision size consideration may refer to a consideration that is based on the size (e.g., length) of one or more incisions made in a patient's body for the purposes of implanting screws into part of the anatomy (e.g., the spine). In some cases, multiple screws may be inserted and implanted through a same incision. Accordingly, evaluating the set of possible screw poses according to an incision size consideration may reduce the size of an individual incision and/or reduce the number of incisions, thereby avoiding unnecessary scarring for the patient.

In at least one example embodiment, the at least one consideration relates to alignment of a rod with at least two screws (e.g., heads of the at least two screws). For example, spinal fusion surgery involves aligning and implanting screws on different pedicles and mechanically coupling the screws to a rod. Thus, evaluating the set of possible screw poses in view of a desired alignment between two or more screws that will mechanically couple to a same rod may be useful for increasing the overall success of the surgery. The alignment consideration may also take the desired curvature of the rod into account, where the desired curvature refers to rod curvature after mechanical coupling to the screws.

In view of the above, it should be appreciated that the at least one consideration may include one or more considerations related to safety of the surgical procedure (e.g., a breach avoidance consideration, a collision avoidance consideration, and the like) in order to reduce the risk of damage to the spine and/or other parts of the anatomy during the surgical procedure. Additionally or alternatively, the at least one consideration includes one or more considerations not related to safety of the surgical procedure. Considerations unrelated to safety of the surgical procedure may include one or more preferences of the surgeon, where such preferences do not have a substantial impact on the risk of damage to the spine or other parts of the anatomy. Such preferences may include preferences related to screw type and/or size, angle of implantation (assuming the angle does not risk damage to the spine or other part of the anatomy), location of implantation (assuming the location does not risk damage to the spine or other part of the anatomy), and/or any other suitable preference that does not involve a substantial risk to safety of the patient or damage to the anatomy of the patient during the surgical procedure. Although preferences of the surgeon are described above as not relating to safety of the surgical procedure, it should be appreciated that the preferences of the surgeon may additionally or alternatively relate to safety of the surgical procedure.

The surgeon may have a subset of preferences within each category of considerations described above (e.g., preferences within a skive avoidance consideration, a breach avoidance consideration, a soft tissue pressure consideration, a collision avoidance consideration regarding possible collisions of a surgical tool with at least one anatomical element in the body, reachability, implant proudness, and/or an incision size consideration). In at least one example embodiment, a surgeon's preferences within some categories are not allowed to violate or exceed certain baseline settings or default criteria while the surgeon's preferences within other categories may be allowed to violate or exceed the baseline settings or default criteria. For example, if breach avoidance is considered important for maintaining safety and/or achieving a desired outcome for the surgery, then the breach avoidance consideration may include a baseline setting that does not allow the method 200 to select a screw pose that will result in a breach (e.g., a medial breach) even if the surgeon's preferences call for allowance of a breach. In addition, the surgeon may be prevented from overriding this setting in the preferences. For example, the surgeon is not provided with the option to select a screw pose and/or is not allowed to alter a selected screw pose that would result or would likely result in a breach.

On the other hand, the incision size consideration may include a default setting that, absent surgeon preferences or external input to the contrary, normally prevents the step 216 from selecting screw poses that result in an incision size larger than a default maximum size. However, in some cases, incision size is a more flexible parameter of the surgical procedure than, for example, breach avoidance. Thus, if the surgeon's preferences include a preference for exceeding the default maximum incision size, the method 200 may perform the evaluation and selection steps 212 and 216 by taking this preference into account. In other words, the method 200 may allow selection of a screw pose that exceeds the default maximum incision size if a surgeon's preference indicates that the default maximum incision size can be exceeded.

As noted above, step 212 may include scoring the set of possible screw poses based on a suitable scale. In this case, one or more of the considerations described above may be weighted according to a desired affect on the selection step 216. For example, in step 212, a consideration that closely correlates with safety and/or effectiveness of the surgical procedure may be weighted more heavily than a consideration that loosely correlates with a safe and/or effective procedure so that step 216 selects a screw pose that is more likely to achieve a safe and/or effective result.

The weights of the one or more considerations may be applied equally across the set of possible screw poses during evaluation. However, example embodiments are not limited thereto, and the weights of the one or more considerations may be applied differently for particular screw poses. For example, a target implant location for a screw may be known to have or suspected of having different risks or potential problems than another target implant location for another screw. In this case, the considerations may be weighted differently for each target implant location to account for the different risks or potential problems at each target implant location.

In at least one example embodiment, the method 200 generates screw pose profiles, where each profile contains a screw pose for multiple screws planned to be implanted. Step 212 may then score and rank each screw pose profile based on weighted and/or unweighted considerations described above. For example, the scores of each screw pose in a screw pose profile are summed together to provide an overall score for the profile. Step 216 may include selecting the screw pose profile with the highest score.

The method 200 may include outputting an indication of the selected at least one screw pose to a user interface (step 220). For example, step 220 outputs an audio and/or visual indication of the selected at least one screw pose to user interface 110. A visual indication of the selected screw pose may include a simulation of implanting the screw into a target implant location on the segmented image generated in step 204. The visual indication may further include additional information about the selected screw pose(s), such as the implant angle, a recommended type and size of screw, and any other suitable information that may be useful for a user to evaluate the selected screw pose(s). The user (e.g., a surgeon) may use the visual indication of the selected screw pose and the other information to evaluate whether the selected screw pose should be applied during the surgical procedure.

Figure 3:
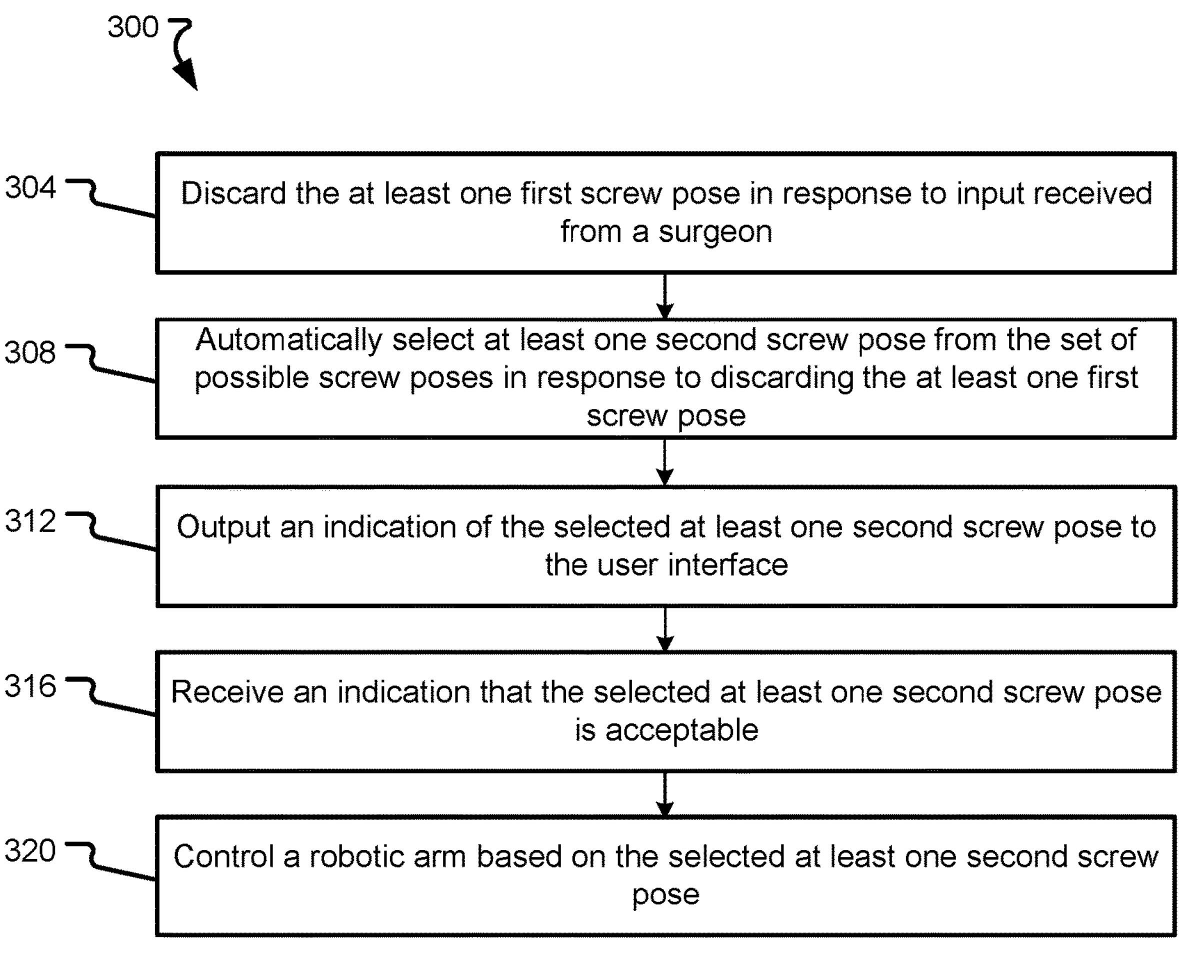
FIG. 3 is a flowchart according to at least one embodiment of the present disclosure.

At this stage, the surgeon may be presented with the opportunity to approve the selected screw pose, reject the selected screw pose, and/or alter the selected screw pose according to additional surgeon preferences or other factors (see FIG. 3 for more detail on screw pose rejection and/or alteration). If the selected screw pose is altered by the surgeon, then the method 200 may further include re-evaluating the altered screw pose as in step 212 to determine whether the altered screw pose creates a potential problem that would cause the altered screw pose to be removed from the selection process in step 216. If so, the method 200 may include outputting a warning message or other indication of the problem to the user interface 110 to inform the surgeon of the potential problem and any relevant information associated with the potential problem (e.g., the altered screw pose increases the risk of collision between a tool and a part of the anatomy). The surgeon can then decide to proceed with the altered screw pose or reject the selected screw pose and/or altered screw pose to prompt the system to output an indication of another screw pose from the set of possible screw poses.

In addition to providing the surgeon with the ability to accept, reject, or alter the selected screw pose, the method 200 may further include providing the surgeon with an updated screw pose that adheres to the surgeon's preferences and/or the surgeon's proposed alteration to the initially selected screw pose. For example, if the surgeon prefers a wider screw than initially proposed by the selected screw pose to improve screw purchase, then the method 200 may include regenerating possible screw poses based on the wider screw and reevaluating those possible screw poses to provide another selected screw pose that takes the wider screw into account. Then, the method 200 may regenerate, reevaluate, and reselect a screw pose for one or more other screws to be implanted during the same surgical procedure (e.g., to maintain rod fit and skin cut alignment).

The method 200 further includes controlling a robotic arm based on the selected at least one screw pose (step 224). For example, the surgeon may determine that the selected screw pose from step 220 (whether altered by the surgeon or not) is an acceptable screw pose for the surgical procedure and provide input on the user interface 110 to apply the selected screw pose during the surgical procedure. For robot assisted surgical procedures, the robotic arm(s) 116 may be controlled to assist with implanting the screw according to the selected screw pose. Such control may include controlling activation and positioning of tooling used to prepare for implantation of the screw (e.g., one or more scalpels, retractors, dilators, a drill, a tap), as well as of tooling used for implantation of the screw itself (e.g., a screwdriver).

The present disclosure encompasses embodiments of the method 200 that comprise more or fewer steps than those described above, and/or one or more steps that are different than the steps described above. For example, steps 204, 220, and/or 224 may be omitted from the method 200 if, for example, these steps are performed by a device external to the system 100. In addition, it should be appreciated that the selected screw pose in step 216 may be stored in the memory 106 and accessed for rendering on a user interface at a later time.

FIG. 3 depicts a method 300 that may be used, for example, to assist with planning implantation of screws in an anatomy such as a spine. The method 300 may be performed in addition to the method 200, for example, as a continuation of the method 200.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing instructions stored in a memory such as the memory 106. The instructions may correspond to one or more steps of the method 300 described below. The instructions may cause the processor to execute one or more algorithms, such as an image processing algorithm 120, a segmentation algorithm 122, a transformation algorithm 124, a registration algorithm 128, and/or a screw planning algorithm 132.

As noted above in the description of FIG. 2, the selected at least one screw pose may be one of many possible screw poses available for selection. For example, upon determining that a selected at least one first screw pose is not acceptable, inventive concepts may proceed to select and present at least one second screw pose different than the selected at least one first screw pose.

Accordingly, the method 300 comprises discarding the at least one first screw pose, for example, in response to input received from a surgeon (step 304). Discarding the at least one first screw pose may include removing the at least one first screw pose from display on the user interface 110, deleting the at least one first screw pose from memory, and/or the like. The input may be received on the user interface 110 and provide an indication to the system 100 that the screw pose output in step 220 is not acceptable to the surgeon. In this case, the method 300 may comprise automatically selecting at least one second screw pose from the set of possible screw poses in response to discarding the at least one first screw pose (step 308). For example, if the first screw pose was selected because it had a highest score among the set of possible screw poses, then step 308 may automatically select a screw pose with a next highest score as the selected screw second pose in step 308. In at least one example embodiment, step 304 includes receiving additional input from the surgeon or user to guide the method 300 in making another selection of a screw pose. Such additional input may include the surgeon's or user's preferences for selecting another screw pose, an indication of why the previously selected screw pose was not acceptable, and/or other suitable input that is useful for increasing the likelihood of the selected second screw pose being approved for use during the surgical procedure.

The method 300 also comprises outputting an indication of the selected at least one second screw pose to the user interface (step 312). For example, step 312 outputs an audio and/or visual indication of the selected at least one second screw pose to user interface 110 in the same or similar manner as that described above with reference to operation 220.

The method 300 includes receiving an indication that the selected at least one second screw pose is acceptable (step 316). For example, the surgeon or user indicates on the user interface 110 that the selected at least one second screw pose is acceptable for use during the surgical procedure. Step 316 may further include allowing the surgeon to make adjustments to the selected at least one second screw pose before indicating that it is acceptable for use in the surgical procedure.

The method 300 further includes controlling a robotic arm based on the selected at least one second screw pose (step 320). Step 320 may be performed in the same or similar manner as step 226 described above. For example, the robotic arm(s) is controlled to implant the at least one screw into the spine according to the selected at least one second screw pose.

The method 300 may be iterated until the selected screw pose is acceptable to the surgeon. Here, it should be appreciated that one or more steps of the method 300 may be performed automatically (e.g., without human intervention). For example, steps 308, 312, and 320 may be performed in response to completion of an immediately preceding step without manual prompting.

The present disclosure encompasses embodiments of the method 300 that comprise more or fewer steps than those described above, and/or one or more steps that are different than the steps described above. For example, steps 312, 316, and 320 may be omitted from the method 300 if, for example, these steps are performed by a device external to the system 100. In addition, it should be appreciated that the screw pose selected in step 308 may be stored in the memory 106 and accessed for rendering on a user interface at a later time to undergo additional steps such as steps 312, 316, and/or 320.

As noted above, the present disclosure encompasses methods with fewer than all of the steps identified in FIGS. 2 and 3 (and the corresponding description of the methods 200 and 300), as well as methods that include additional steps beyond those identified in FIGS. 2 and 3 (and the corresponding description of the methods 200 and 300). The present disclosure also encompasses methods that comprise one or more steps from one method described herein, and one or more steps from another method described herein. Any correlation described herein may be or comprise a registration or any other correlation.

Although example embodiments have been shown and described with respect to screw planning for spinal surgeries, it should be appreciated that example embodiments may also cover planning for screws in other types of surgeries. In addition, example embodiments are also relevant to planning poses for surgical fixing devices other than screws, which may include staples, pins, rods, plates, stitches, and/or the like.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device comprising:

at least one processor; and memory including instructions that when executed by the at least one processor cause the at least one processor to:

generate, based on at least one image of a spine within a body, a set of possible screw poses for a screw to be implanted into a target location of the spine during a surgical procedure;

evaluate each possible screw pose for the screw to be implanted into the target location based on a plurality of considerations associated with the surgical procedure, at least one consideration of the plurality of considerations having a default setting normally applied to the surgical procedure and a preference setting set by a surgeon prior to performing the surgical procedure, wherein evaluating each possible screw pose includes:

determining, for each of the at least one consideration, whether the preference setting is allowed to override the default setting based on how important the default setting is to achieving a desired outcome of the surgical procedure;

excluding, from the set of possible screw poses, possible screw poses which have the preference setting that is not allowed to override the default setting to yield a subset of possible screw poses for the screw to be implanted into the target location;

select a screw pose from the subset of possible screw poses for the screw to be implanted into the target location; and control a robotic arm based on the selected screw pose.

2. The device of claim 1, wherein the instructions include instructions that when executed by the at least one processor cause the at least one processor to:

output an indication of the selected screw pose to a user interface; and prevent, for the selected screw pose, the surgeon from manually overriding the default setting for each of the at least one consideration.

3. The device of claim 1, wherein the instructions include instructions that when executed by the at least one processor cause the at least one processor to:

generate the at least one image by segmenting at least one three-dimensional image of the spine.

4. The device of claim 1, wherein the plurality of considerations include one or more considerations related to safety of the surgical procedure.

5. The device of claim 1, wherein the plurality of considerations include at least two of a skive avoidance consideration, a breach avoidance consideration, a soft tissue pressure consideration, a collision avoidance consideration regarding possible collisions of a surgical tool with at least one anatomical element in the body, reachability, implant proudness, or an incision size consideration.

6. The device of claim 1, wherein the plurality of considerations include one or more considerations not related to safety of the surgical procedure.

7. The device of claim 1, wherein the plurality of considerations include at least one second consideration with a preference setting set by the surgeon that performs the surgical procedure.

8. The device of claim 1, wherein the screw is included in a plurality of screws, and wherein selecting the screw pose selects a screw pose for each of the plurality of screws.

9. The device of claim 8, wherein the plurality of considerations relate to alignment of a rod with at least two screws of the plurality of screws, wherein the at least two screws mechanically couple to the rod.

10. The device of claim 1, wherein the evaluation includes scoring each of the possible screw poses in the subset of screw poses based on the plurality of considerations, and wherein the screw pose is selected based on the scoring.

11. The device of claim 10, wherein the plurality of considerations relate to safety of the surgical procedure, preferences of the surgeon performing the surgical procedure, and a desired alignment of a rod with the screw.

12. The device of claim 1, wherein at least one of the plurality of considerations is weighted.

13. A system comprising:

a user interface;

at least one processor; and memory including instructions that when executed by the at least one processor cause the at least one processor to:

generate, based on at least one image of a spine within a body, a set of possible screw poses for implanting a screw into a target location of the spine during a surgical procedure;

evaluate each possible screw pose for the screw to be implanted into the target location based on a plurality of considerations associated with the surgical procedure, at least one consideration of the plurality of considerations having a default setting normally applied to the surgical procedure and a preference setting set by a surgeon prior to performing the surgical procedure, wherein evaluating each possible screw pose includes:

determining, for each of the at least one consideration, whether the preference setting is allowed to override the default setting based on how important the default setting is to achieving a desired outcome of the surgical procedure;

excluding, from the set of possible screw poses, possible screw poses which have the preference setting that is not allowed to override the default setting to yield a subset of possible screw poses for the screw to be implanted into the target location;

select, based on the evaluation, a first screw pose from the subset of possible screw poses for the screw to be implanted into the target location;

output a first indication of the selected first screw pose to the user interface;

receive a second indication of whether the selected first screw pose is acceptable, the second indication corresponding to first user input received on the user interface; and control a robotic arm based on the second indication.

14. The system of claim 13, wherein the instructions include instructions that cause the at least one processor to:

adjust the selected first screw pose based on second user input while preventing the default setting from being overridden for each of the at least one consideration.

15. The system of claim 14, wherein the second user input includes surgical preferences for performing the surgical procedure.

16. The system of claim 13, wherein the instructions include instructions that cause the at least one processor to:

discard the selected first screw pose in response to the second indication indicating that the selected first screw pose is not acceptable;

automatically select a second screw pose from the subset of possible screw poses in response to discarding the selected first screw pose; and output a third indication of the selected second screw pose to the user interface.

17. The system of claim 16, further comprising:

the robotic arm, wherein the instructions include instructions that cause the at least one processor to:

receive a fourth indication corresponding to second user input indicating that the selected second screw pose is acceptable; and control the robotic arm based on the selected second screw pose.

18. The system of claim 17, wherein the robotic arm is controlled to implant the screw into the spine according to the selected second screw pose.

19. The system of claim 13, wherein the plurality of considerations include considerations relating to safety of the surgical procedure, preferences of the surgeon performing the surgical procedure, and a desired alignment of a rod with the first screw.

20. A method, comprising:

generating, based on at least one segmented image of a spine within a body, a set of possible screw poses for implanting a screw into a target location of the spine during a surgical procedure;

evaluating each possible screw pose for the screw to be implanted into the target location based on a plurality of considerations associated with the surgical procedure, at least one consideration of the plurality of considerations having a default setting normally applied to the surgical procedure and a preference setting set by a surgeon prior performing the surgical procedure, wherein evaluating each possible screw pose includes:

determining, for each of the at least one consideration, whether the preference setting is allowed to override the default setting based on how important the default setting is to achieving a desired outcome of the surgical procedure;

excluding, from the set of possible screw poses, possible screw poses which have the preference setting that is not allowed to override the default setting to yield a subset of possible screw poses for the screw to be implanted into the target location;

selecting, based on the evaluation, a first screw pose from the subset of possible screw poses for the screw to be implanted into the target location; and controlling a robotic arm based on the selected first screw pose.

* * * * *